United States Patent [19]
Fukui et al.

[11] Patent Number: 5,148,806
[45] Date of Patent: Sep. 22, 1992

[54] ELECTRODE FOR USE WITH A LIVING BODY

[76] Inventors: Yasuhiro Fukui; Kazuyuki Mitsui, both of 2-2, Nisiki-Cho, Kanda, Chiyoda-Ku, Tokyo 101; Hiroshi Kato; Yoshihiro Chikamori, both of 123, Minamigata, Yoshinaga-Cho, Wake-Gun, Okayama-Ken 709-02, all of Japan

[21] Appl. No.: 456,113

[22] Filed: Dec. 22, 1989

[30] Foreign Application Priority Data

Dec. 23, 1988 [JP] Japan ............................... 63-325510

[51] Int. Cl.⁵ ................................................ A61B 5/04
[52] U.S. Cl. .................................. 128/639; 128/784; 128/640; 128/798
[58] Field of Search ............................... 128/634–641, 128/643–644, 798, 802, 803, 784–786

[56] References Cited

U.S. PATENT DOCUMENTS

| | | | |
|---|---|---|---|
| 3,590,810 | 7/1971 | Kopecky | 128/640 |
| 3,602,216 | 8/1971 | Moe | 128/640 |
| 4,187,390 | 2/1980 | Gore . | |

FOREIGN PATENT DOCUMENTS

| | | |
|---|---|---|
| 0008460 | 8/1979 | European Pat. Off. . |
| 0275628 | 9/1987 | European Pat. Off. . |
| 2045088 | 3/1980 | United Kingdom . |
| 2179555 | 8/1986 | United Kingdom . |

*Primary Examiner*—Kyle L. Howell
*Assistant Examiner*—Scott L. Akers
*Attorney, Agent, or Firm*—Wayne D. House

[57] ABSTRACT

An electrode for use primarily in electrocardiography is described. This electrode is comprised of porous polytetrafluoroethylene and an electrically conductive powder so as to be moisture vapor permeable. A preferred embodiment uses fibrillized porous polytetrafluoroethylene. It may have an adhesive on one surface for easy attachment to a patient.

15 Claims, 7 Drawing Sheets

ELECTRODE FOR USE WITH A LIVING BODY

FIELD OF THE INVENTION

The present invention concerns an electrode for use in stimulation and the measurement of electric potentials of a living body in electrocardiography, etc.

BACKGROUND OF THE INVENTION

In the case of electrodes conventionally used for the measurement of electric potentials of the human body (as in the case of electrocardiographic electrodes) or for stimulation in pacemakers and therapy, etc., the electrodes are retained on the surface of the skin by suction, using a suction disk at each measurement position on the body (e.g., thorax, etc.). Specifically, the electrodes are set in place following a pre-treatment in which the surface of the skin is coated with a conductive jelly, etc.

Furthermore, a system is also used in which the electrodes are fixed in place by means of adhesive tape. In such cases, the electrodes used are generally metal electrodes.

In the case of the above mentioned conventional electrodes using suction disks, there are difficulties in electrode retention (e.g., in cases where the negative pressure of the suction disks is weak, the suction force may be lost as a result of slight movements of the body or perspiration, etc.). Accordingly, it is difficult to perform electrocardiographic measurements over a long period of time using such electrodes. Furthermore, as a result of the need to apply a conductive jelly, etc., to the surface of the skin in order to improve the conductivity of the suction attachment, the setting of the electrodes on the body takes time, which is especially inconvenient in emergency cases.

Furthermore, if the negative pressure of the suction disks is too strong, subcutaneous hemorrhaging may occur (in the chest wall, etc.). Accordingly, there are unavoidable limitations on the negative pressure that can be used.

In cases where adhesive tape is used, reddening of the skin commonly occurs. This gives the patient an unpleasant sensation, and the patient commonly experiences discomfort in the case of long-term recording.

Furthermore, in the case of conventional metal electrodes, there is a feeling of weight when the electrodes are applied to the measurement positions on the skin. Since such electrodes are rigid and therefore do not readily conform to the contours of the skin surface, the effective contact area is limited. Furthermore, such electrodes may easily slip off.

SUMMARY OF THE INVENTION

The present invention relates to an electrode for use on a living body, comprised of a material containing 5 to 90 percent by weight polytetrafluoroethylene and 10 to 95 percent by weight conductive powder, said material having been made porous.

In a preferred embodiment, said material has been made porous by fibrillation, producing a microstructure of nodes interconnected by fibrils, so that fine gaps are formed between the fibrils produced by this fibrillization, and so that the nodes interconnected by these fibrils are substantially connected to each other.

BRIEF DESCRIPTION OF THE DRAWINGS

The attached figures illustrate the technical content of the present invention.

In these figures, (1) indicates an electrode, (2) indicates the adhesive part of said electrode, (3) indicates a differential amplifier, (4) indicates a human heart, (5) indicates a connecting part, (6) indicates a cord, and (7) indicates a connector.

DETAILED DESCRIPTION OF THE INVENTION

Electrode material of the present invention, containing 5 to 90 percent by weight polytetrafluoroethylene and 10 to 95 percent by weight conductive powder is made porous by any suitable pore-forming technique that is capable of creating void spaces within the material. The pores should be of adequate size to allow the passage of water vapor. An electrode of such material is soft, flexible, water vapor permeable, and is reduced in weight compared to conventional electrode materials.

The preferred electrode material is made by a fibrillization process that produces a microstructure of nodes interconnected by fine fibrils. The aforementioned conductive powder collects in these node portions, so that the concentration of said powder is enriched in said node portions.

Since the above mentioned nodes are substantially connected to each other, electrical conduction is obtained from the areas of enriched conductive powder concentration formed as described above. Accordingly, the material has an appropriate effect as an electrode for measuring electric potentials.

As a result of the above mentioned softness, moisture vapor permeability, flexibility and weight reduction, a state of stable and reliable adhesion to the body surface is obtained, and this state is maintained.

As a result of the above mentioned polytetrafluoroethylene content of 5 percent by weight or greater (and preferably 20 percent by weight or greater), the above mentioned fibrillized portions can be effectively formed. Furthermore, in regard to the above mentioned upper limit of 90 percent by weight (and preferably 70 percent by weight) of this polytetrafluoroethylene content, said limit is set in order to allow the admixture of 10 percent by weight or more (and preferably 30 percent by weight or more) conductive powder, so that an electrical conductivity appropriate for an electrode can be obtained.

The electrode of the present invention may be made in various shapes, e.g., round, square, rectangular, etc. One surface may be partly or completely coated with a suitable adhesive to allow the electrode to adhere stably to the skin. Additionally, the electrode may be made to have a connecting part which projects from one side in order to facilitate the connection of lead wires, etc.

Any method suitable for forming pores or void spaces within the PTFE/conductive powder material may be used to create the product of the present invention so long as pores of a size adequate to pass moisture vapor are created. For example, a powder with a pore-forming action can be mixed with the conductive powder, and pores can be formed by removing this pore-forming agent (by heating or extraction by solvent, etc.) following the molding process.

In the preferred embodiment of the present invention, a material formed by mixing a conductive powder with a polytetrafluoroethylene resin (hereafter referred to as "PTFE") is fibrillized by a rolling or drawing treatment, so that large numbers of fibrils and nodes are formed into a microstructure wherein the fibrils interconnect numerous small nodes which are substantially connected to each other, and the resulting sheet material is used as an electrode.

The above mentioned fibrillized material is generally produced by the following processes (1) through (6):

(1) A mixture formed by adding a conductive powder and a liquid lubricant to finely powdered PTFE is kneaded into a paste-form substance.

(2) This paste-form substance is then formed into a sheet (or tube, or rod) by compression, extrusion, drawing or rolling, or by a combination of two or more of these processes. These processes initially fibrillize the material.

(3) The liquid lubricant is removed from the above mentioned molding by heating or extraction, etc.

(4) Next, if necessary, the above mentioned molding is subjected to a drawing or rolling treatment in at least one direction, so that said molding is further fibrillized. This is preferably done while heating the molding to a temperature less than the crystalline melt point of PTFE.

(5) In cases where most of the fine nodes formed as a result of the above mentioned fibrillization are separated from each other, a further compression treatment may be performed so that said nodes are connected to each other to a substantial degree. This step is performed if a reduction in porosity or increase in density or conductivity is desired.

(6) The material obtained as a result of the above mentioned processes (1) through (3), (1) through (4) or (1) through (5) is sintered at a temperature greater than the crystalline melt point of PTFE.

Furthermore, the above mentioned process (5) is performed by means of pressing plates or rolls, etc., and this process (5) may be performed following the above mentioned process (6).

The above mentioned processes (1) through (6) are generally described in U.S. Pat. Nos. 3,953,566, 3,962,153 and 4,187,390. These patents describe porous expanded fibrillized PTFE in which the expansion occurs during process (4) described above. If the material is not subjected to step (4) above, then it is not considered an expanded material, however, it is still considered fibrillized.

The conductive powder used in the above mentioned process (1) is generally a carbonaceous powder such as carbon black or graphite, etc. However, it would also be possible to use metals such as gold, tantalum or titanium, etc., oxides of such metals, or powdered Raney metals, etc. Such substances may be used singly or in mixtures.

It is desirable that the aforementioned conductive powder have a mean particle diameter of 10 microns or less. A powder with a mean particle diameter exceeding 10 microns causes difficulties in working in processes such as the above mentioned processes (2) and (3), so that reliable fibrillization and pore size adjustment become difficult to achieve. Furthermore, the amount of conductive powder used in the material is 10 percent by weight or greater (preferably 30 percent by weight or greater, and even more preferably 40 to 80 percent by weight). In this way, the volume resistivity of the material can be lowered to 1.0 ohm-cm or less.

Examples of liquid lubricants which can be used in order to form the above mentioned paste, and in order to convert said paste into a sheet, include (for the above mentioned PTFE) liquid hydrocarbons such as petroleum, solvent naptha and white oil, etc., and other substances such as ethylene glycol, glycerine, water, polyethylene oxide and phthalic acid esters, etc. The amount of liquid lubricant used is generally 18 to 220 percent by weight relative to the amount of PTFE used. Kneading and adjustment can be performed using appropriate universally known methods. If desired, waxes or other materials which enhance water-repelling properties may be added as supplementary raw materials.

A sheet with, for example, a fibril length of 0.08 to 22 microns, a density of 0.18 to 1.15 g/cm$^3$ and a Gurley number of 0.9 seconds or greater can be reliably obtained as described above.

Furthermore, it was confirmed by microscopic observation that in the conversion of the aforementioned material into a porous material by a drawing process such as the above mentioned process (4), most of the conductive powder mixed with the material collects in the node portions. Powder also adheres to the surfaces of the fibrils. Since the node portions are in contact with each other or connected to each other, an electrical conductivity appropriate for an electrode can be reliably obtained. Especially in cases where a fine carbon powder with a particle size of 0.1 microns or less (e.g., carbon black, etc.) is used, such a structure can be obtained by using an excess of liquid lubricant and performing the aforementioned processes (1) through (3) (without any need to perform the processes from (4) on. Furthermore, conductive powder adhering to the surfaces of the fibrils can be brought into close contact by applying an appropriate compression treatment process (5) either before or after the heat treatment process (6) following the above mentioned drawing treatment process (4), so that the above mentioned electrical conductivity is reinforced. Furthermore, in cases where such a compression treatment results in an insufficient gas permeability, holes which pass through the material can be formed by laser working or discharge working, etc.

Concrete examples of manufacture of the present invention will be described below.

EXAMPLE 1

A mixture consisting of 40 percent by weight of powdered PTFE and 60 percent by weight conductive carbon black (Ketchen Black EC) was prepared. 70 parts by weight of a liquid lubricant was mixed with 100 parts by weight of the above mentioned mixture so that a paste-form mixture was obtained. This paste-form mixture was temporarily molded into a cylindrical shape, and was then formed into a sheet with a thickness of 0.12 mm by compression, paste extrusion and rolling. Next, this sheet was fixed so that it would not shrink in the direction of rolling, and was heated in this state so that the liquid lubricant was removed (and so that dimensional stability was insured). In this way, an electrode material was obtained. The volume resistivity of this electrode material was 0.5 ohm-cm, and the Gurley number (indicating gas permeability) was 80 seconds.

Figure 1:
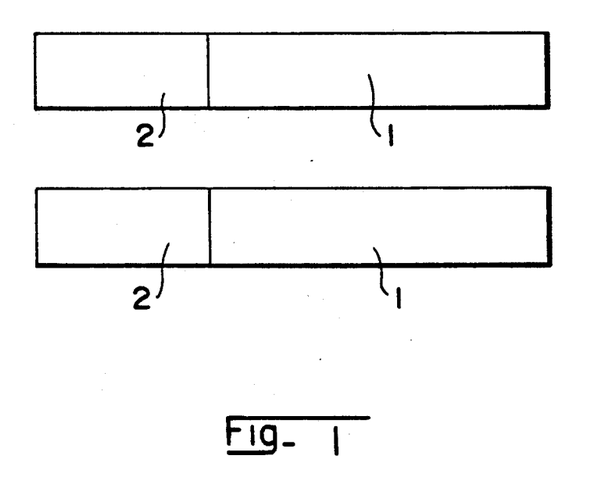
FIG. 1 is a plan view which illustrates an example of electrodes constructed according to the present invention.
Figure 2:
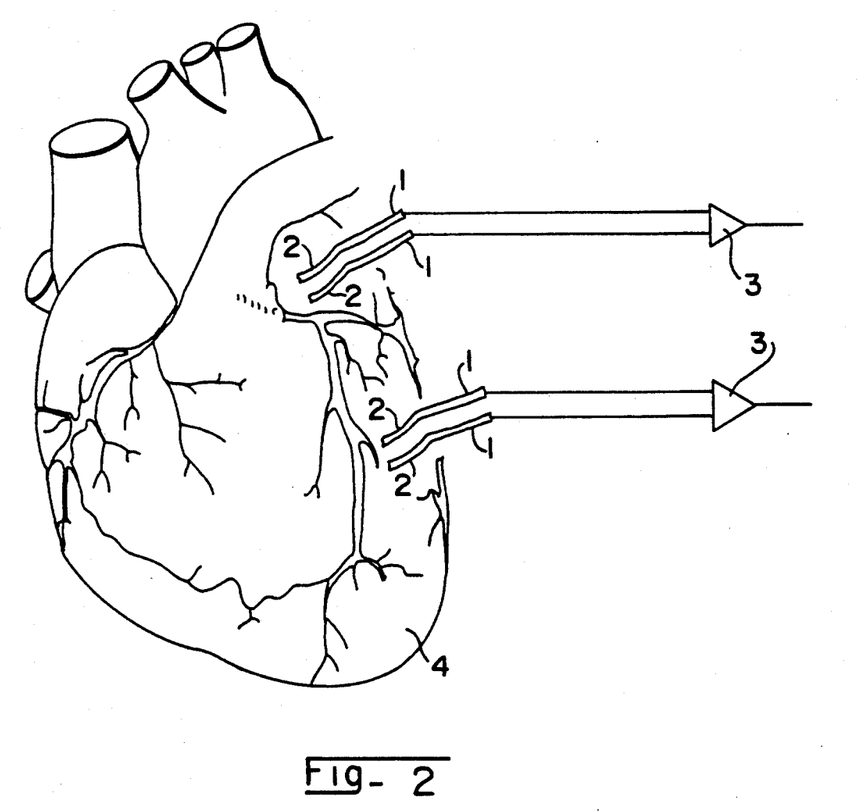
FIG. 2 is an explanatory diagram which illustrates the conditions of measurement when the above mentioned electrodes are applied to the heart.
Figure 3:
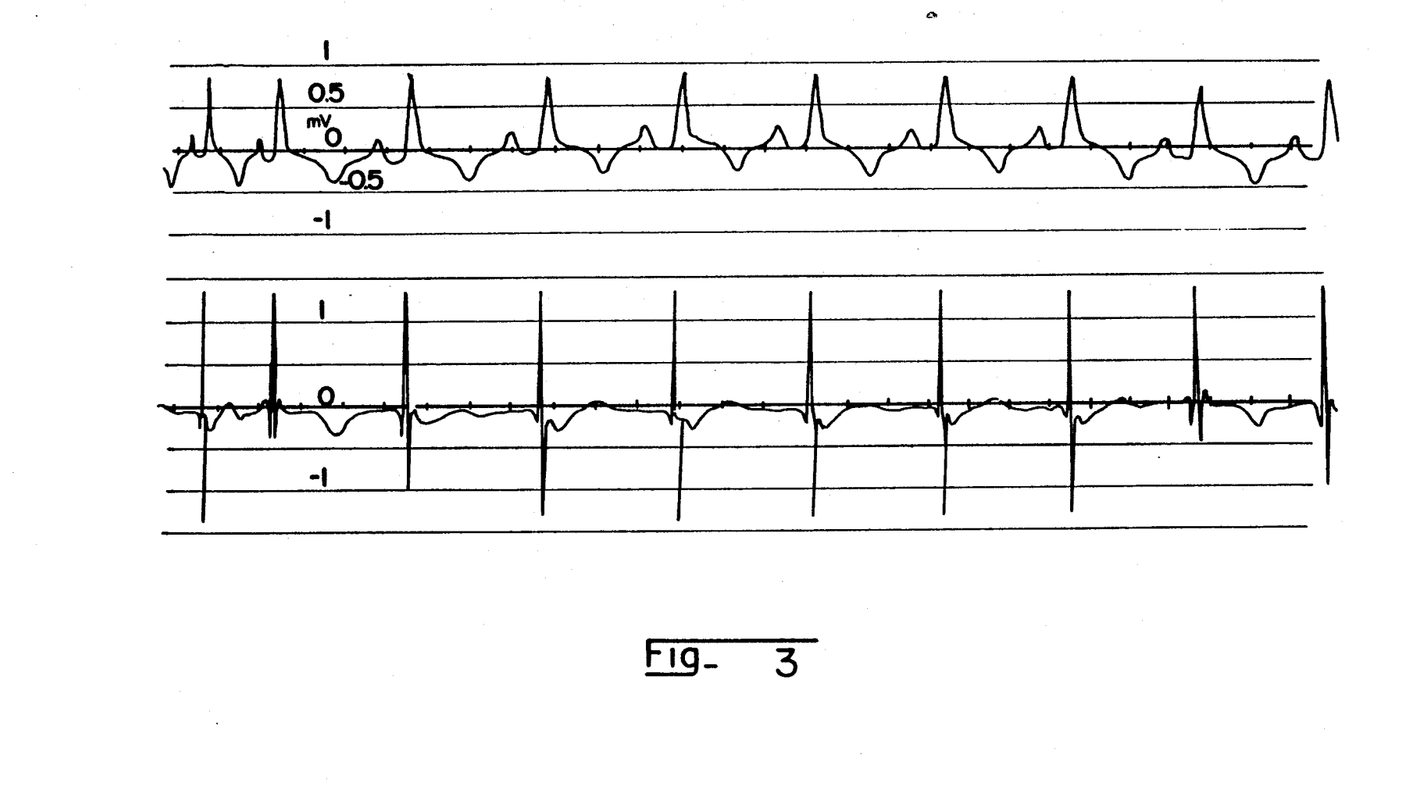
FIGS. 3 and 4 are graphs which show the results of the above mentioned measurements.
Figure 4:
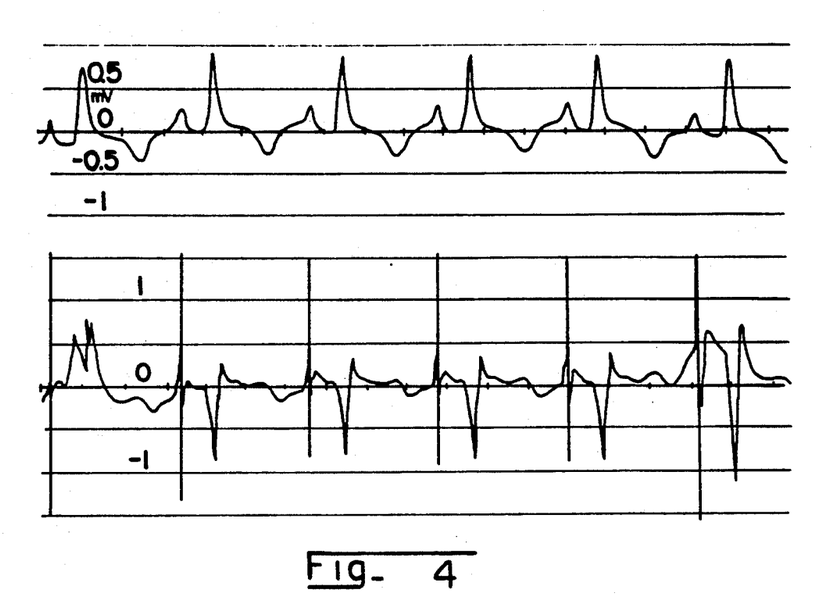

The electrode material obtained as described above was formed into electrodes (1) with a width of 5 mm and a length of 30 mm as shown in FIG. 1. One end portion of each electrode (1) was used as an adhesive part (2) (with a length of 10 mm). The opposite ends of two pairs of said electrodes (1, 1) were connected to differential amplifiers (3) as shown in FIG. 2, and were applied to the left ventricle and left atrium of the heart (4) area so that respective bipolar arrangements were obtained. The waveforms from the respective electrodes were input using the differential amplifiers (3). The left ventricle and left atrium area results obtained are shown respectively in FIGS. 3 and 4.

Figure 5:
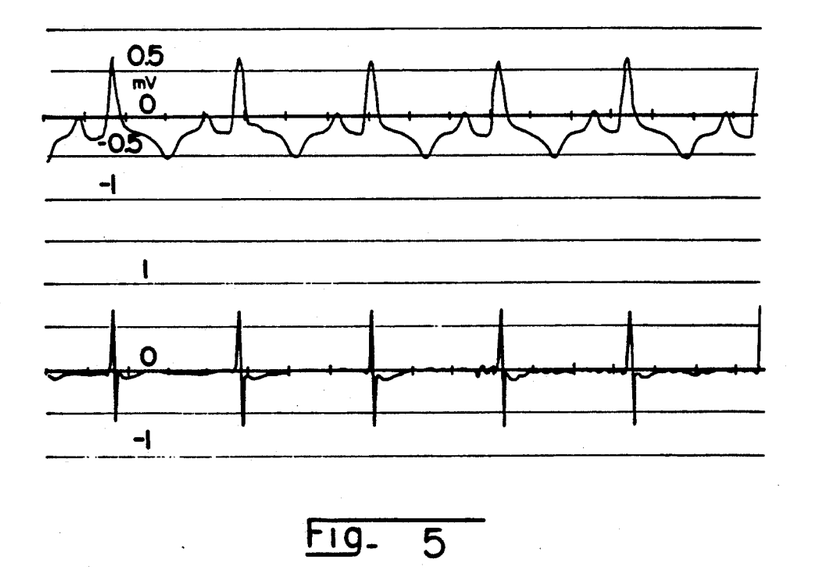
FIGS. 5 and 6 show similar measurement results obtained using conventional copper electrodes.
Figure 6:
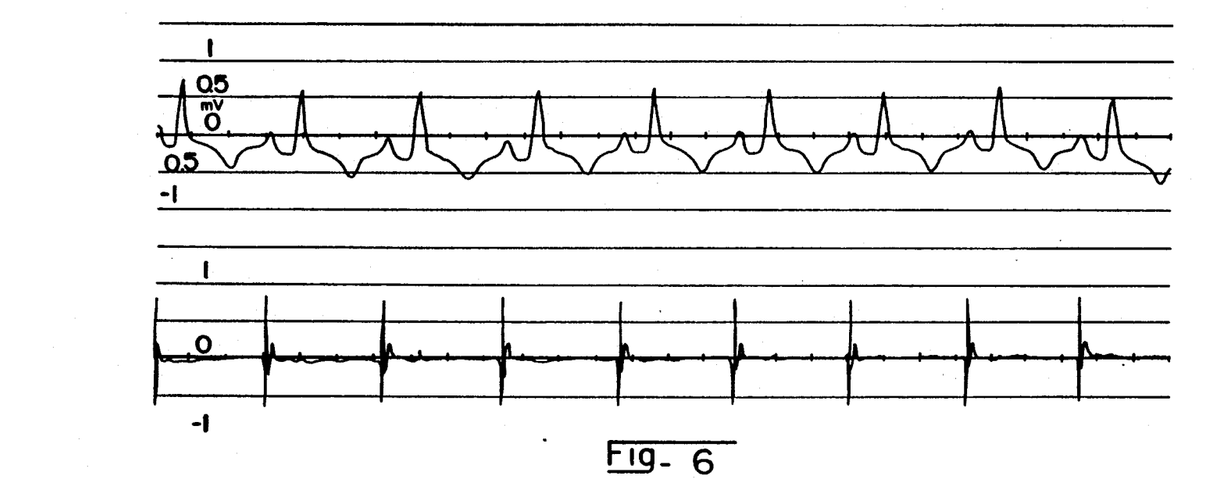

Furthermore, in comparison to the waveforms obtained using the present invention as described above, activity potential waveforms for the right ventricle and right atrium area obtained by means of bipolar electrode arrangements using conventional copper electrodes are as shown respectively in FIGS. 5 and 6.

Specifically, in the above mentioned FIGS. 3 through 6, electrocardiographic waveforms obtained from electrodes placed on the right wrist and left foot are shown in the upper portion of each figure, and activity waveforms obtained from the electrodes placed over the heart area as described are shown in the lower portion of each figure. It is clear that the electrodes of the present invention produce measurement results that are equal to or better than the measurement results obtained using conventional cooper electrodes.

The electrodes (1) shown in FIG. 1 have a simple rectangular shape. However, in a desirable configuration of the present invention, the adhesive part (2) of each electrode (1) is formed in the shape of a square whose width is greater than the width of the remainder of the electrode (1).

Furthermore, the electrodes provided by the present invention have a desirable moisture vapor permeability, so that faulty adhesion due to perspiration, etc., can be avoided.

EXAMPLE 2

Figure 7:
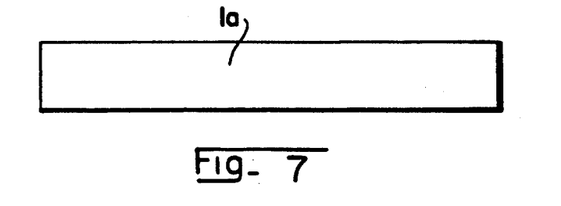
FIG. 7 is a plan view which illustrates another electrode of the present invention.
Figure 8:
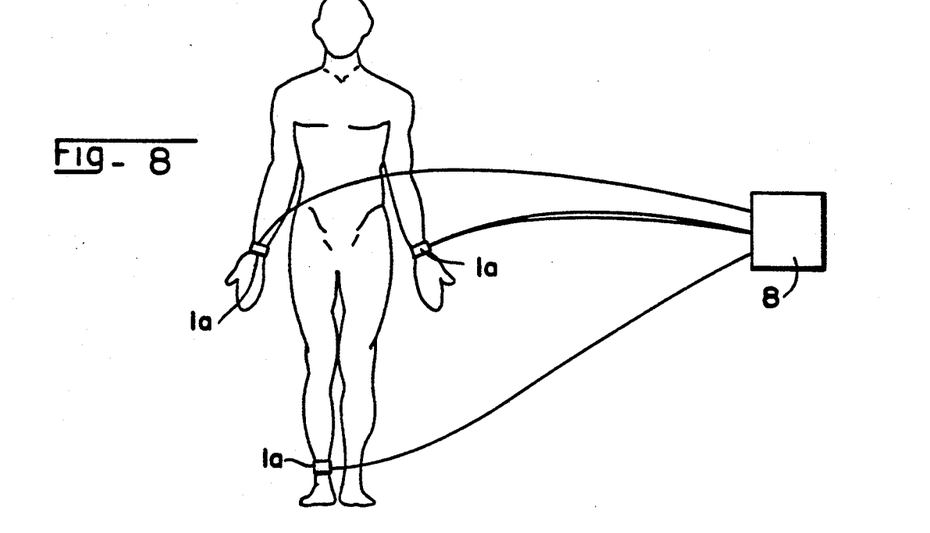
FIG. 8 is an explanatory diagram which illustrates the conditions of measurement in a case where electrodes of the type shown in FIG. 7 are applied to the right arm, left arm and right ankle of a patient.

Using the electrode material obtained in Example 1, an electrode (1a) for application by wrapping around the ankles and wrists as shown in FIG. 8, was manufactured as shown in FIG. 7 (width of electrodet 15 mm, length of electrodet 225 mm).

Figure 9:
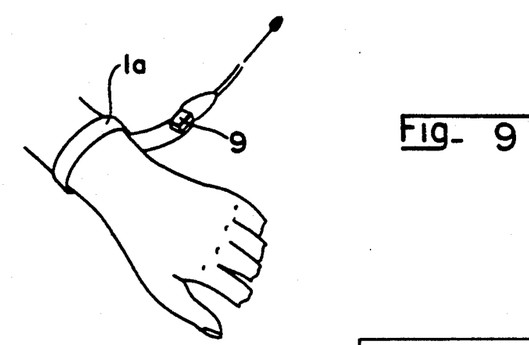
FIG. 9 is an explanatory diagram which illustrates the connection of electrodes of the present invention to an electrocardiograph by means of alligator clips.
Figure 10:
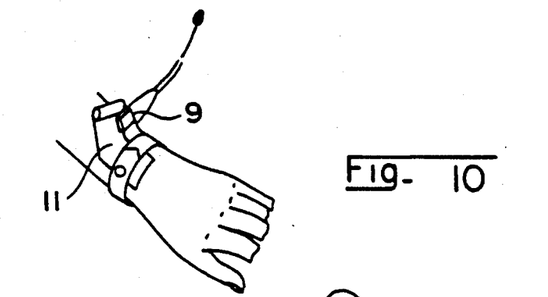
FIG. 10 is an explanatory diagram which illustrates the connection of comparative metal electrodes to an electrocardiograph by means of alligator clips.
Figure 11A:
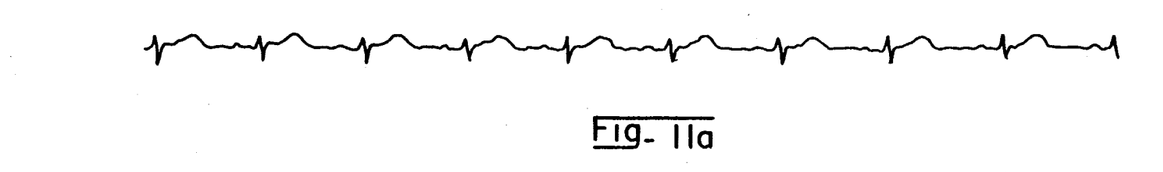
FIGS. 11a and 11b are graphs showing electrocardiographic measurement results obtained using electrodes of the present invention and electrocardiographic measurement results obtained using the above mentioned comparative metal electrodes.
Figure 11B:
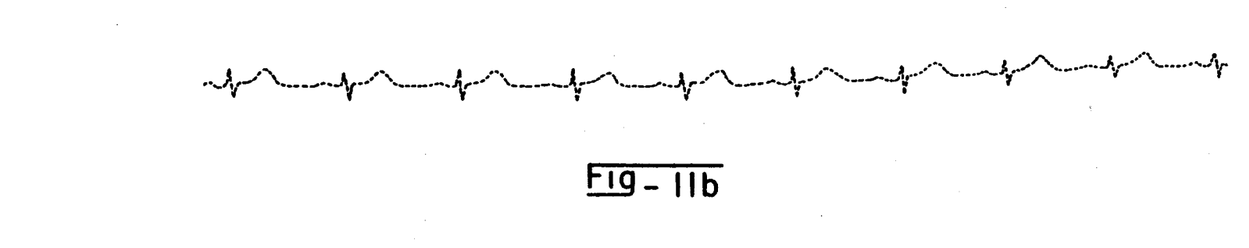

Samples of this electrode (1a) were wrapped around the right arm, left arm and right ankle of a person as shown in FIG. 8, and each of the electrodes was connected to an electrocardiograph by means of an alligator clip as shown (for example) in FIG. 9. An electrocardiogram was measured using this electrode arrangement. Separately, metal electrodes (1) prepared as a comparative example were connected by means of alligator clips (9) as shown in FIG. 10, and an electrocardiogram was recorded using this arrangement as well. The results obtained are compared in FIG. 11a showing the results from the inventive electrodes in FIG. 11b) showing the results from the comparative electrodes. It is seen that the present invention produced measurement results that were equal to or better than the measurement results produced by the comparative example.

Furthermore, in these measurements, it was confirmed that the electrodes of the present invention do not require the use of a conductive jelly (which is necessary in the case of the above mentioned comparative metal electrodes). Instead, it is sufficient if a small amount of physiological saline solution is placed between the electrodes and the body. Such an arrangement eliminates the unpleasant sensation experienced by the patient in cases where a conductive jelly is used. Furthermore, peeling of the electrodes due to perspiration, which is a problem in the case of conventional electrodes, is completely eliminated in the case of the present invention. On the contrary, it was confirmed that perspiration actually increases the degree of contact between the electrodes and the skin in the case of the present invention.

EXAMPLE 3

Figure 12:
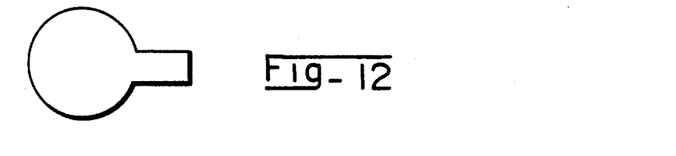
FIG. 12 is a plan view which illustrates another electrode of the present invention.
Figure 13:
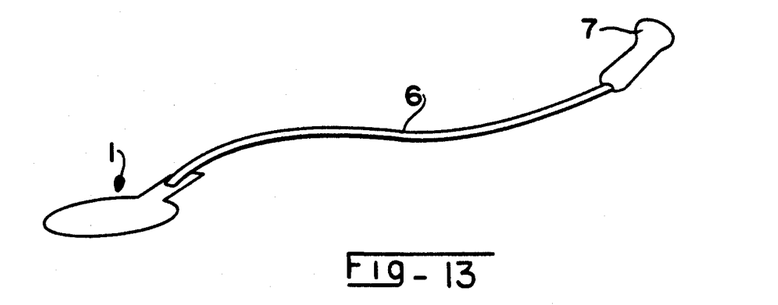
FIG. 13 is an explanatory diagram which illustrates the connection of a cord for disposable electrocardiographic electrodes to the electrode shown in FIG. 12.

Using an electrode material obtained in the same manner as in Example 1, an electrode (1) was prepared which had a connecting part (5) with a width of 5 mm and a length of 10 mm projecting from one side of an adhesive part (2) formed in the shape of a flat circle with a diameter of 20 mm, as shown in FIG. 12. An electrocardiographic electrode was obtained by connecting a cord (6) and connector (7) (used with disposable electrocardiographic electrodes) to the connecting part (5) of the above mentioned electrode (1) as shown in FIG. 13.

Electrodes (1) produced as described above were attached to the skin of the right hand and left foot (ground) of a patient, and an electrocardiogram was taken. In this case, the attachment of the electrodes was accomplished using physiological saline in one experiment and a conductive jelly in a second experiment. Furthermore, electrocardiographic electrodes made of metal were separately prepared as a comparative example., these electrodes were attached using a conductive jelly, and similar measurements were performed.

Figure 14A:
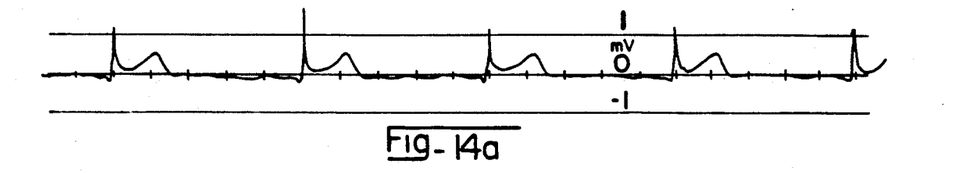
FIG. 14 is a graph which illustrates electrocardiographic measurement results obtained using electrodes of the type shown in FIGS. 12 and 13 (using physiological saline and a conductive jelly in separate experiments) and electrocardiographic measurement results obtained using comparative metal electrodes (with a conductive jelly).
Figure 14B:
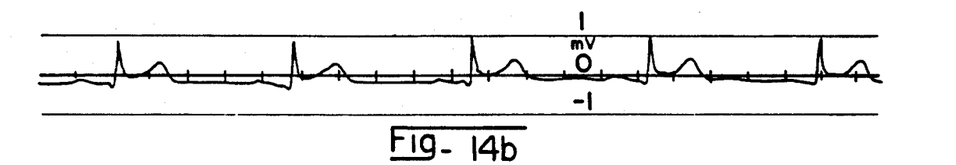
Figure 14C:
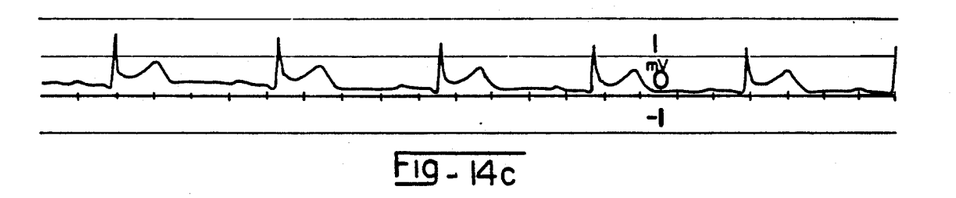

The measurement results obtained are shown in FIGS. 14a–14c wherein FIG. 14a shows the results obtained when the electrodes of the present invention were attached using physiological saline, FIG. 14b indicates the results obtained when the electrodes of the present invention were attached using a conductive jelly, and FIG. 14c shows the results obtained when the comparative metal electrodes were attached using a conductive jelly. It is seen that these measurement results show virtually no difference. This demonstrates that effective measurement results can be obtained even in cases where electrodes of the present invention are attached using physiological saline.

Furthermore, in regard to the shape of the adhesive part (2) in the electrode shown in FIG. 12, it is not absolutely necessary that said part be perfectly circular in shape; in some cases, the part may be formed in the shape of an ellipse or oval, etc. Moreover, the connecting part (5) may be of any desired shape, as long as it prevents the adhesive part from being affected by the connected cord.

I claim:

1. A conductive electrode for use on a living body, comprised of a porous, water vapor permeable material containing 5 to 90 percent by weight polytetrafluoroethylene and 10 to 95 percent by weight conductive powder.

2. A conductive electrode according to claim 1 wherein said porous, water vapor permeable material has a microstructure of nodes interconnected by fibrils, wherein void spaces exist between the fibrils, and the nodes interconnected by these fibrils are substantially connected to each other.

3. A conductive electrode according to claim 2 having been made porous by a fibrillization process.

4. A conductive electrode according to claims 1, 2 or 3 wherein said conductive powder is carbon black.

5. A conductive electrode according to claims 1, 2 or 3 wherein said conductive powder is a metal.

6. A conductive electrode according to claims 1, 2 or 3 having at least one side, an upper surface and a lower surface, wherein said lower surface is at least partly coated with an adhesive.

7. A conductive electrode according to claims 1, 2 or 3 which is rectangular in shape.

8. A conductive electrode according to claims 1, 2 or 3 which is square in shape.

9. A conductive electrode according to claim 8 which has a connecting part projecting from one side.

10. A conductive electrode according to claims 1, 2 or 3 which is circular in shape.

11. A conductive electrode according to claim 10 which has a connecting part projecting from one side.

12. A conductive electrode according to claims 1, 2 or 3 which is elliptical in shape.

13. A conductive electrode according to claim 12 which has a connecting part projecting from one side.

14. A conductive electrode according to claim 1 comprised of a porous, water vapor permeable material containing 20 to 70 percent by weight polytetrafluoroethylene and 30 to 80 percent by weight conductive powder.

15. A conductive electrode according to claim 1 comprised of a porous, water vapor permeable material containing 20 to 60 percent by weight polytetrafluoroethylene and 40 to 80 percent by weight conductive powder.

* * * * *